US00PP36657P2

(12) United States Plant Patent
Koning

(10) Patent No.: US PP36,657 P2
(45) Date of Patent: May 6, 2025

(54) ***CURIO* PLANT NAMED 'Stelvio'**

(50) Latin Name: *Curio ficoides*
Varietal Denomination: Stelvio

(71) Applicant: Koning & Koning B.V., Westerbork (NL)

(72) Inventor: Geu Koning, Westerbork (NL)

(73) Assignee: Koning & Koning B.V. (NL)

( * ) Notice: Subject to any disclaimer, the term of this patent is extended or adjusted under 35 U.S.C. 154(b) by 0 days.

(21) Appl. No.: 18/823,410

(22) Filed: Sep. 3, 2024

(30) Foreign Application Priority Data

Sep. 19, 2023 (QZ) ..... PBR 2023/1871

(51) Int. Cl.
*A01H 5/12* (2018.01)
*A01H 6/14* (2018.01)

(52) U.S. Cl.
USPC ..... Plt./373

(58) Field of Classification Search
USPC ..... Plt./373, 480
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct variety of *Curio* plant named 'Stelvio' is disclosed, characterized by a neat, upright, and compact growth habit, and dense, full foliage with thick, strong stems. The new variety is a *Curio*, typically produced as ornamental plants.

3 Drawing Sheets

Latin name of the genus and species: *Curio ficoides.*
Variety denomination: 'STELVIO'.

BACKGROUND OF THE INVENTION

The new cultivar, *Curio* 'Stelvio', is the product of a planned breeding program by the inventor. *Curio* 'Stelvio' is the result of a September 2019 open-pollination of the seed parent, *Senecio ficoides* 'Mount Everest', U.S. Plant Pat. No. 22,188, and various unidentified *Curio ficoides* pollen parent varieties. The new cultivar, *Curio* 'Stelvio' was discovered by the inventor in 2020 in Paterswolde, the Netherlands at a commercial greenhouse.

Asexual reproduction of the new cultivar 'Stelvio' was first performed at a greenhouse in Paterswolde, the Netherlands, by vegetative cuttings in 2021. 'Stelvio' has since produced multiple generations and has shown that the unique features of this cultivar are stable and reproduced true to type.

SUMMARY OF THE INVENTION

The cultivar 'Stelvio' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Stelvio' These characteristics in combination distinguish 'Stelvio' as a new and distinct *Curio* cultivar:

1. Dense, full foliage.
2. Neat and upright growth habit.
3. Thick, strong stems.
4. Compact plant habit.

PARENT COMPARISON

Plants of the new cultivar 'Stelvio' are similar to plants of the seed parent in most horticultural characteristics, however, plants of the new cultivar 'Stelvio' differ in the following;

1. Growth habit of the new variety is neater and more even than the growth habit of the seed parent.
2. Foliage of the new variety is denser than foliage of the seed parent.
3. Plants of the new variety are more compact than plants of the seed parent.
4. Stems of the new variety are stronger, thicker, and better branched than stems of the seed parent.

COMMERCIAL COMPARISON

Plants of the new cultivar 'Stelvio' are comparable to the commercial variety *Curio ficoides* 'Blues', U.S. Plant Pat. No. 34,480. The two *Curio* varieties are similar in most horticultural characteristics; however, the new variety 'Stelvio' differs in the following:

1. Stems of the new variety are stronger, thicker, and better branched than stems of this comparator.
2. Plants of the new variety are more compact and rounder than plants of this comparator.
3. Foliage of the new variety is denser than foliage of this comparator.
4. Internodes of the new variety are shorter than internodes of this comparator.

BRIEF DESCRIPTION OF THE PHOTOGRAPHS

The accompanying photograph in FIG. 1 illustrates in full colour a typical plant of 'Stelvio' in a 27 cm pot. Age of the plant photographed is approximately 1 year old.

Figure 1:
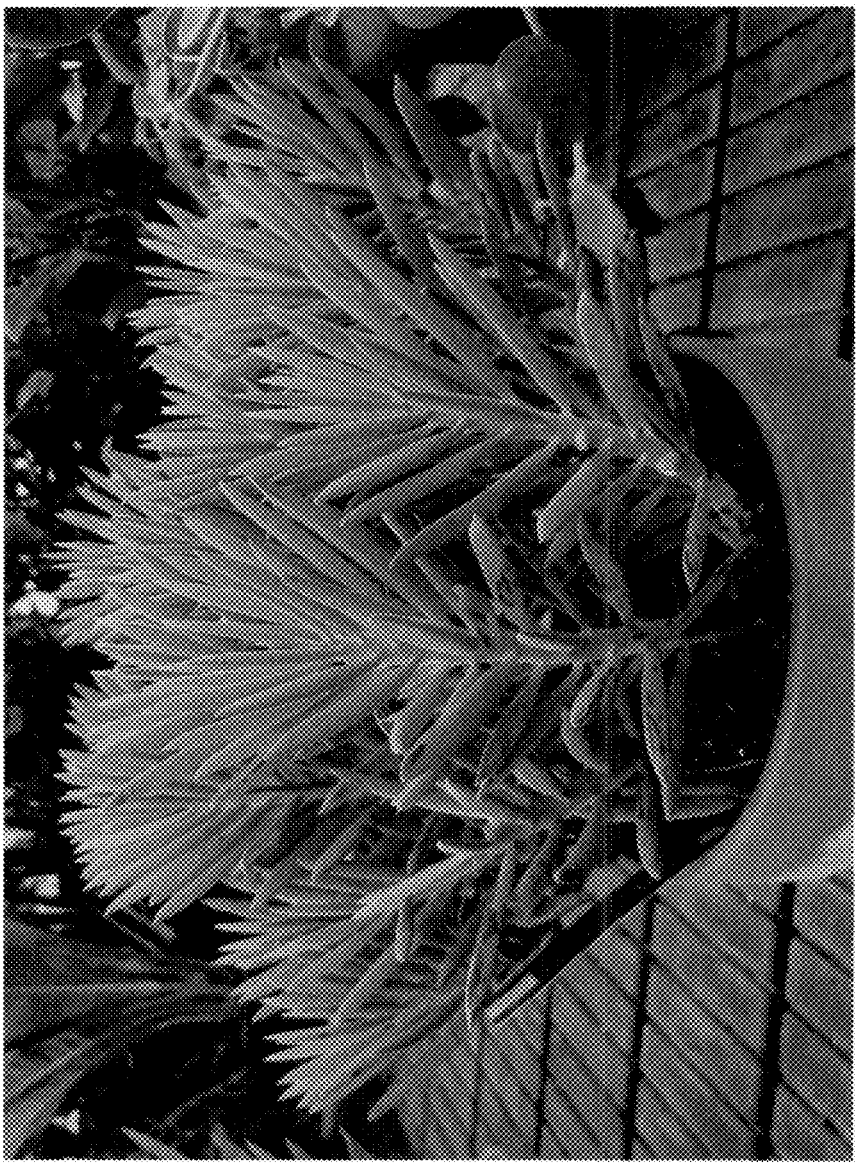
Figure 2:
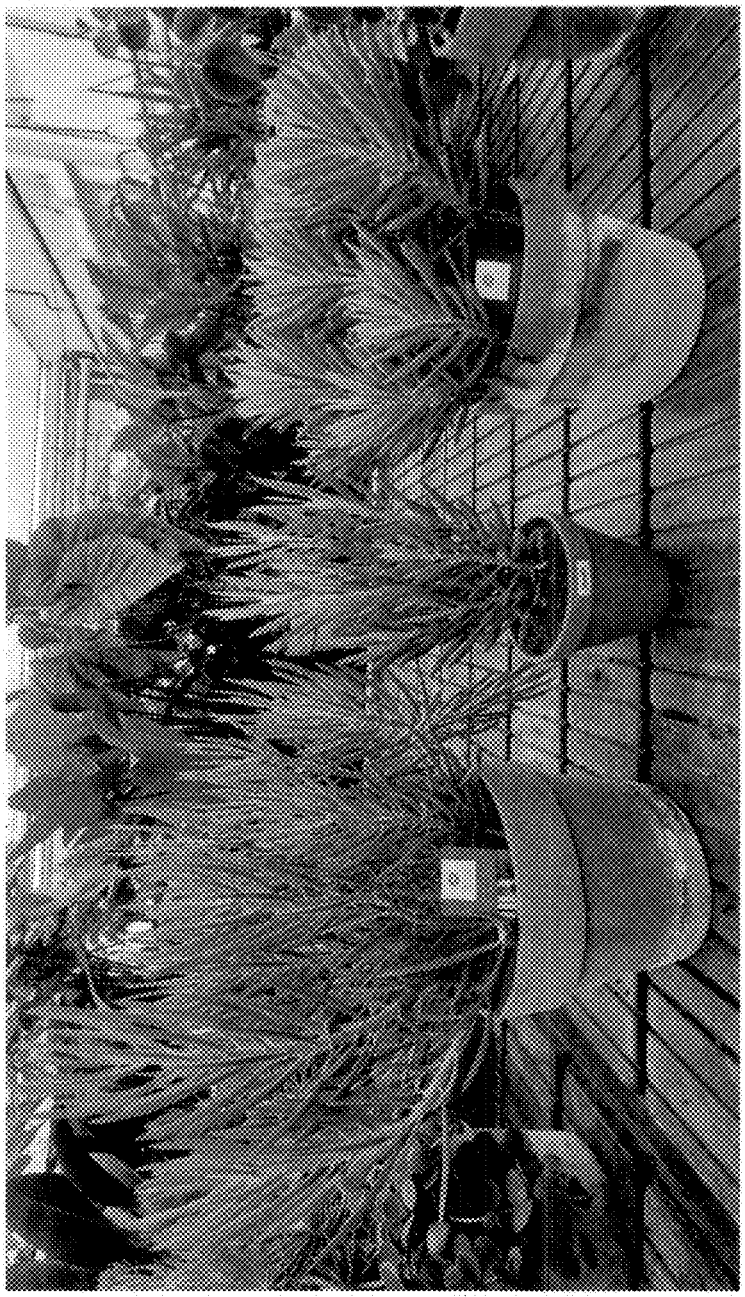
FIG. 2 illustrates a comparison of plants of the new variety(on the right of the photograph, the parent variety (center) and comparator 'Blues'(left).
Figure 3:
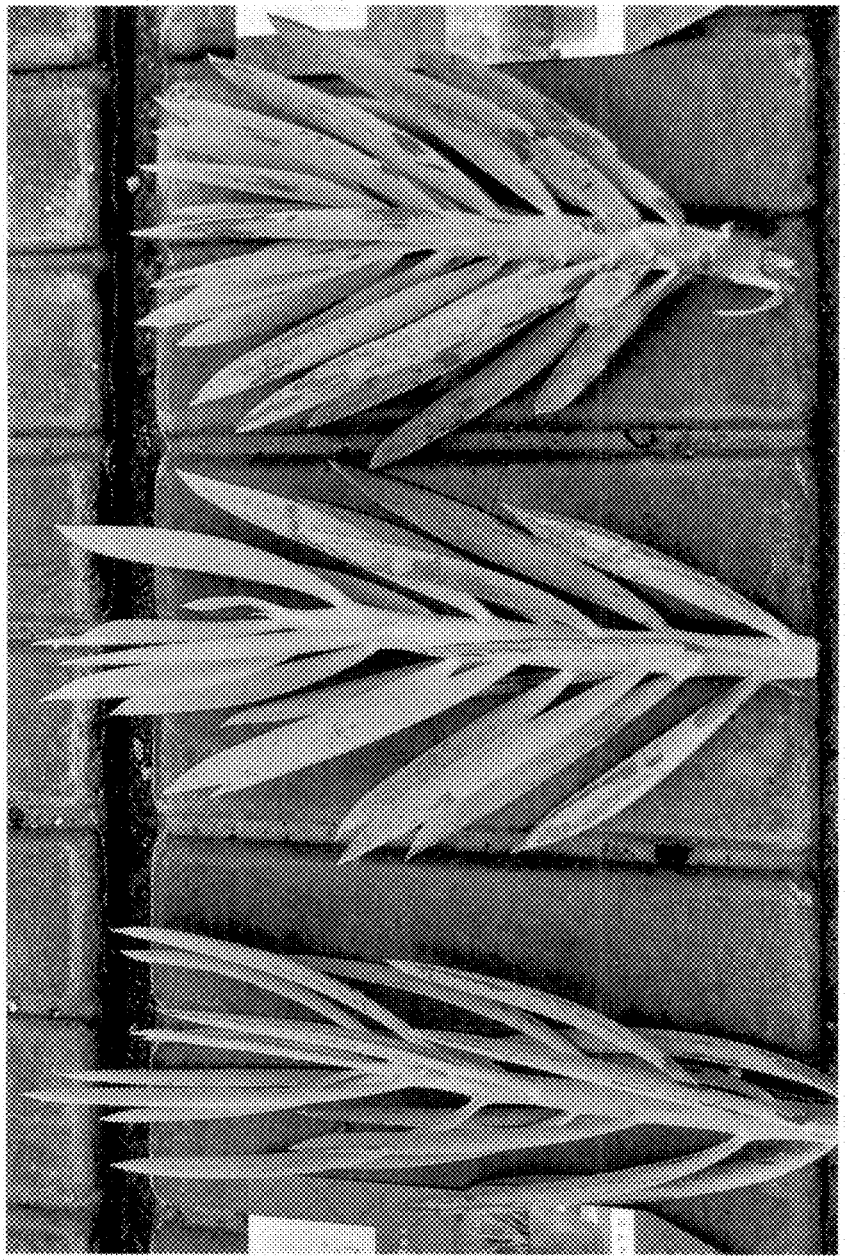
FIG. 3 illustrates a comparison of a typical stem and foliage of the new variety(on the right of the photograph, the parent variety(center) and comparator 'Blues'(left).

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'Stelvio' plants grown indoors in Paterswolde, the Netherlands. Temperatures ranged from about 5° C. to 29° C. No artificial light, photoperiodic treatments or chemical treatments were given to the plants. Measurements and numerical values represent averages of typical plant types.

Botanical classification: *Curio ficoides* 'STELVIO'.

PROPAGATION

Type of propagation typically used: Terminal vegetative cuttings.

PLANT

Age of plant described: Approximately 1 year.
Container size of the plant described: 17 cm pot.
Growth habit: Compact and upright.
Height: 25 cm.
Plant spread: 25 cm.
Stem:
- *Quantity*.—12 per plant.
- *Length*.—40 cm.
- *Width*.—Up to 2 cm.
- *Color*.—RHS Green NN137A with a waxy layer near Greyed-Green 188A.
- *Texture*.—Glabrous, glaucous.
- *Strength*.—Moderate.
- *Internode*.—4 mm or less.

FOLIAGE

Leaf:
- *Quantity*.—About 60 to 70 per lateral stem.
- *Length*.—8 cm.
- *Width*.—1 cm.
- *Shape*.—Gladiate.
- *Cross-section shape*.—Triangular.
- *Apex*.—Acute,
- *Base*.—Truncate.
- *Margin*.—Entire.
- *Texture*.—Glabrous, waxy.
- *Color*.—Young leaves, upper and lower: Near RHS Yellow-Green 144A at the base. More towards Green 137C from the middle to the top. Waxy layer close to Greyed-Green 188A flushed with Blue 122C. Mature leaves, upper and lower: RHS Yellow-Green 144A at the base (small part), Green NN137A in the center and towards the top. Waxy layer close to Greyed-Green 188A flushed with Blue 122C.

FLOWER

Flowering not observed to date.

REPRODUCTIVE ORGANS

Unknown, as flowering has not been observed.

OTHER CHARACTERISTICS

Fruits and seeds: Not observed.
Temperature tolerance: Tolerates temperatures from approximately 2° C. to 32° C.
Disease/pest resistance: No increased nor decreased resistance to normal diseases and pests of *Curio* has been observed.

What is claimed is:

1. A new and distinct cultivar of *Curio* plant named 'STELVIO' as herein illustrated and described.

* * * * *